US008727983B2

(12) United States Patent
Kinnison

(10) Patent No.: US 8,727,983 B2
(45) Date of Patent: May 20, 2014

(54) SYSTEMS AND METHODS FOR MAKING AND USING A CONDUCTIVE-FLUID DETECTOR FOR A CATHETER-BASED MEDICAL DEVICE

(75) Inventor: Charlotte F. Kinnison, Clarkdale, AZ (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 603 days.

(21) Appl. No.: 12/855,546

(22) Filed: Aug. 12, 2010

(65) Prior Publication Data
US 2011/0040162 A1   Feb. 17, 2011

Related U.S. Application Data

(60) Provisional application No. 61/233,957, filed on Aug. 14, 2009.

(51) Int. Cl.
| A61M 5/172 | (2006.01) |
| A61M 5/44 | (2006.01) |
| A61B 18/02 | (2006.01) |
| A61N 7/02 | (2006.01) |

(52) U.S. Cl.
USPC ............. 600/371; 600/345; 600/584; 604/27; 604/43; 604/65; 604/66; 604/67; 604/96.01; 604/113; 604/114; 604/264; 606/20; 606/21; 606/22; 606/23; 606/24; 606/25; 606/26; 606/27; 606/28; 606/29; 606/33; 606/41

(58) Field of Classification Search
USPC .......... 600/371, 584, 345; 606/33, 41, 20–29; 604/27, 43, 65, 66, 67, 96.01, 113, 604/114, 264
See application file for complete search history.

(56) References Cited

U.S. PATENT DOCUMENTS

| 3,993,945 | A | 11/1976 | Warmoth |
| 4,380,237 | A | 4/1983 | Newbower |
| 6,463,331 | B1* | 10/2002 | Edwards ................. 607/101 |
| 6,666,858 | B2 | 12/2003 | Lafontaine |
| 6,755,822 | B2 | 6/2004 | Reu et al. |
| 6,905,493 | B2 | 6/2005 | Lentz |
| 7,101,368 | B2 | 9/2006 | Lafontaine |
| 7,189,227 | B2 | 3/2007 | Lafontaine |
| 2005/0228367 | A1* | 10/2005 | Abboud et al. .............. 606/20 |
| 2007/0161980 | A1* | 7/2007 | Young et al. ................ 606/41 |

(Continued)

FOREIGN PATENT DOCUMENTS

| DE | 4137628 | 12/1992 |
| WO | 2008091610 | 2/2011 |

*Primary Examiner* — Jacqueline Cheng
*Assistant Examiner* — Puya Agahi
(74) *Attorney, Agent, or Firm* — Seager, Tufte & Wickhem, LLC

(57) ABSTRACT

A catheter-based medical device includes a catheter that is configured and arranged for at least partial insertion into a patient and that defines at least one lumen that is configured and arranged to receive a first fluid. A conductive-fluid detector is coupled to the at least one lumen and is configured and arranged to detect when a second fluid is disposed within the at least one lumen that is more conductive than the first fluid. The conductive-fluid detector includes a plurality of axially-positioned bodies, each body defining a lumen. The lumens of the axially-positioned bodies are aligned to form a shared lumen in fluid communication with the at least one lumen of the catheter. Spaced apart electrodes are disposed within the shared lumen.

20 Claims, 8 Drawing Sheets

(56) References Cited

U.S. PATENT DOCUMENTS

| | | | |
|---|---|---|---|
| 2008/0039727 A1* | 2/2008 | Babaev | 600/471 |
| 2008/0039791 A1* | 2/2008 | Abboud et al. | 604/113 |
| 2008/0161796 A1* | 7/2008 | Cao et al. | 606/41 |
| 2008/0221508 A1* | 9/2008 | Abboud et al. | 604/30 |
| 2008/0300571 A1* | 12/2008 | LePivert | 604/503 |
| 2009/0182318 A1* | 7/2009 | Abboud et al. | 606/21 |
| 2009/0287201 A1* | 11/2009 | Lalonde et al. | 606/21 |
| 2010/0041986 A1* | 2/2010 | Nguyen et al. | 600/427 |
| 2010/0168557 A1* | 7/2010 | Deno et al. | 600/424 |
| 2010/0174169 A1* | 7/2010 | Razavi | 600/371 |
| 2010/0210934 A1* | 8/2010 | Belson | 600/371 |
| 2010/0286684 A1* | 11/2010 | Hata et al. | 606/33 |

* cited by examiner

SYSTEMS AND METHODS FOR MAKING AND USING A CONDUCTIVE-FLUID DETECTOR FOR A CATHETER-BASED MEDICAL DEVICE

CROSS-REFERENCE TO RELATED APPLICATIONS

This application claims the benefit of U.S. Provisional Application No. 61/233,957, filed Aug. 14, 2009, the entire disclosure of which is incorporated herein by reference.

TECHNICAL FIELD

The present invention is directed to the area of medical ablation systems and methods of making and using the medical ablation systems. The present invention is also directed to medical ablation systems having conductive-fluid detectors for monitoring for the presence of conductive fluids in non-conductive environments, as well as systems and methods for making and using the medical ablation systems and conductive-fluid detectors.

BACKGROUND

Medical ablation systems (e.g., cryoablation systems, radio-frequency ablation systems, or the like) have proven therapeutic. Cryoablation systems can be used to form cold-induced lesions on patient tissue. Cryoablation systems have been used to reduce, or even eliminate, undesired electrical activity between adjacent cardiac tissues of the heart (arrhythmias). Radio frequency ablation systems ("RF ablation systems") use microwave energy to form heat-induced lesions on patient tissue and can also be used to treat some of the same conditions as cryoablation systems, including arrhythmias.

One common type of arrhythmia, atrial fibrillation, is a result of abnormal electrical signals interfering with the normal electrical signal propagation along the tissues of the heart. Atrial fibrillation often originates near the ostia of the pulmonary veins. Mapping catheters can be used to locate the abnormal electrical signals and medical ablation systems ("ablation systems") can be used to form lesions on patient tissue through which the abnormal electrical signals are propagated (e.g., tissue along the inner walls of the ostia (where the pulmonary veins open into the left atrium of the heart), or in proximity to the ostia). The cold-induced (or heat-induced) lesions can effectively block the initiation or propagation of the abnormal electrical signals, thereby preventing the abnormal electrical signals from interfering with the normal electrical signal propagation along the tissues of the heart.

BRIEF SUMMARY

In one embodiment, a catheter-based medical device includes a catheter and a conductive-fluid detector. The catheter is configured and arranged for at least partial insertion into a patient. The catheter defines at least one lumen that is configured and arranged to receive a first fluid. The conductive-fluid detector is coupled to the at least one lumen and is configured and arranged to detect when a second fluid is disposed within the at least one lumen that is more conductive than the first fluid. The conductive-fluid detector includes a first electrode, a second electrode, and a fluid pathway that is coupled to the at least one lumen of the catheter and that is configured and arranged to receive the first electrode and the second electrode. The first electrode has a proximal end, a distal end, an inner surface, and an outer surface. The second electrode also has a proximal end, a distal end, an inner surface, and an outer surface. The fluid pathway includes a plurality of axially-positioned bodies, each body having an inner surface and defining a lumen. The lumens are aligned to form a shared lumen in fluid communication with the at least one lumen of the catheter. The fluid pathway also includes a first elongated body having a proximal end disposed over the distal end of the outer surface of the first electrode such that the distal end of the outer surface of the first electrode couples to the inner surface of the first elongated body and the inner surface of the first electrode is disposed in the shared lumen. The fluid pathway further includes a second elongated body having a distal end disposed over the proximal end of the outer surface of the second electrode such that the proximal end of the outer surface of the second electrode couples to the inner surface of the second elongated body and the inner surface of the second electrode is disposed in the shared lumen. Additionally, the fluid pathway includes a connecting body having a proximal end and a distal end. The distal end of the inner surface of the connecting body is coupled to the proximal end of the outer surface of the first electrode and the proximal end of the inner surface of the connecting body is coupled to the distal end of the outer surface of the second electrode such that the first electrode and the second electrode are electrically separated from one another.

In another embodiment, a medical ablation device includes an ablation catheter, a guide tube, an ablation element, and a conductive-fluid detector. The ablation catheter has a distal portion, a proximal portion, and a longitudinal length. The ablation catheter is configured and arranged for insertion into patient vasculature. The ablation catheter includes a body and defines at least one coolant outtake region extending along at least a portion of the ablation catheter. The at least one coolant outtake region defines at least one lumen configured and arranged to receive a coolant. The guide tube is at least partially disposed in the ablation catheter. The ablation element is coupled to the distal portion of the body of the ablation catheter. The ablation element is configured and arranged for ablating patient tissue. The conductive-fluid detector is coupled to the at least one coolant outtake region and is configured and arranged to detect when a second fluid is disposed within the at least one lumen of the at least one coolant outtake region that is more conductive than the coolant. The conductive-fluid detector includes a first electrode, a second electrode, and a fluid pathway that is coupled to the at least one coolant outtake region and that is configured and arranged to receive the first electrode and the second electrode. The first electrode has a proximal end, a distal end, an inner surface, and an outer surface. The second electrode also has a proximal end, a distal end, an inner surface, and an outer surface. The fluid pathway includes a plurality of axially-positioned bodies, each body having an inner surface and defining a lumen. The lumens are aligned to form a shared lumen in fluid communication with the at least one lumen of the at least one coolant outtake region. The fluid pathway also includes a first elongated body having a proximal end disposed over the distal end of the outer surface of the first electrode such that the distal end of the outer surface of the first electrode couples to the inner surface of the first elongated body and the inner surface of the first electrode is disposed in the shared lumen. The fluid pathway further includes a second elongated body having a distal end disposed over the proximal end of the outer surface of the second electrode such that the proximal end of the outer surface of the second electrode couples to the inner surface of the second elongated body and the inner surface of the second electrode is disposed in the shared lumen. Additionally, the fluid pathway includes a connecting body having a proximal end and a distal end. The distal end of the inner surface of the connecting body is coupled to the proximal end of the outer surface of the first electrode and the proximal end of the inner surface of the connecting body is coupled to the distal end of the outer surface of the second electrode such that the first electrode and the second electrode are electrically separated from one another.

In yet another embodiment, a method of detecting blood in a catheter-based medical device includes inserting at least a portion of the catheter-based medical device into a patient. The catheter-based medical device includes a catheter that defines at least one lumen and a conductive-fluid detector coupled to the lumen. The conductive-fluid detector includes a first electrode, a second electrode, and a fluid pathway coupled to the lumen of the catheter and configured and arranged to receive the first electrode and the second electrode. The first electrode has a proximal end, a distal end, an inner surface, and an outer surface. The second electrode has a proximal end, a distal end, an inner surface, and an outer surface. The fluid pathway includes a plurality of axially-positioned bodies. Each body has an inner surface and defines a lumen. The lumens of the fluid pathway are aligned to form a shared lumen with the at least one lumen of the catheter. The fluid pathway also includes a first elongated body having a proximal end disposed over the distal end of the outer surface of the first electrode such that the distal end of the outer surface of the first electrode couples to the inner surface of the first elongated body and the inner surface of the first electrode is disposed in the shared lumen. The fluid pathway further includes a second elongated body having a distal end disposed over the proximal end of the outer surface of the second electrode such that the proximal end of the outer surface of the second electrode couples to the inner surface of the second elongated body and the inner surface of the second electrode is disposed in the shared lumen. Additionally, the fluid pathway includes a connecting body having a proximal end and a distal end. The distal end of the inner surface of the connecting body is coupled to the proximal end of the outer surface of the first electrode and the proximal end of the inner surface of the connecting body is coupled to the distal end of the outer surface of the second electrode such that the first electrode and the second electrode are electrically separated from one another. A first fluid is passed along the at least one lumen of the catheter such that the first fluid passes through the fluid pathway and between the first annular electrode and the second annular electrode. At least one electrical parameter is monitored between the first annular electrode and the second annular electrode within the lumen of the connecting body when the first fluid passes between the first annular electrode and the second annular electrode.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of medical ablation systems and methods of making and using the medical ablation systems. The present invention is also directed to medical ablation systems having conductive-fluid detectors for monitoring for the presence of conductive fluids in non-conductive environments, as well as systems and methods for making and using the medical ablation systems and conductive-fluid detectors.

Conductive-fluid detectors are described herein for use with cryoablation systems. It will be understood, however, that conductive-fluid detectors may be used with other types of ablation systems as well including, for example, RF ablation systems. It will also be understood that conductive-fluid detectors may also be used with other types of medical devices including, for example, catheter-based medical devices configured and arranged for at least partial insertion into a patient. Conductive-fluid detectors may also be used with non-medical devices in which the detection of a conductive fluid in a normally non-conductive or minimally conductive fluid path is desired, for example, the detection of sea water.

Suitable cryoablation systems include, but are not limited to, an expansion element disposed on a distal end of an ablation catheter configured and arranged for percutaneous insertion into a patient. Examples of cryoablation systems with ablation catheters are found in, for example, U.S. Pat. Nos. 7,189,227; 7,101,368; 6,905,493; 6,755,822; and 6,666,858, all of which are incorporated by reference.

A cryoablation system can include an ablation catheter configured and arranged for transporting coolant to and from a target location within a patient, an expansion element disposed at a distal portion of the ablation catheter for ablating contacted patient tissue, a coolant source coupled to the ablation catheter for supplying the coolant, and a control module for controlling or monitoring one or more of the operations of the system (e.g., controlling coolant flow, monitoring ablation catheter pressure or temperature, or the like). The expansion element can be positioned at a target location in patient vasculature (e.g., the left atrium of the heart) and the coolant can be input to the ablation catheter and directed to the expansion element. When the coolant contacts the expansion element, the coolant absorbs heat and expands, thereby causing the expansion element to expand and reduce in temperature to a level low enough to ablate patient tissue upon contact. The coolant flows out of the expansion element and back to a proximal end of the ablation catheter. As the coolant flows out of the expansion element, the expansion element deflates and the ablation catheter may be removed from the patient vasculature.

Figure 1:
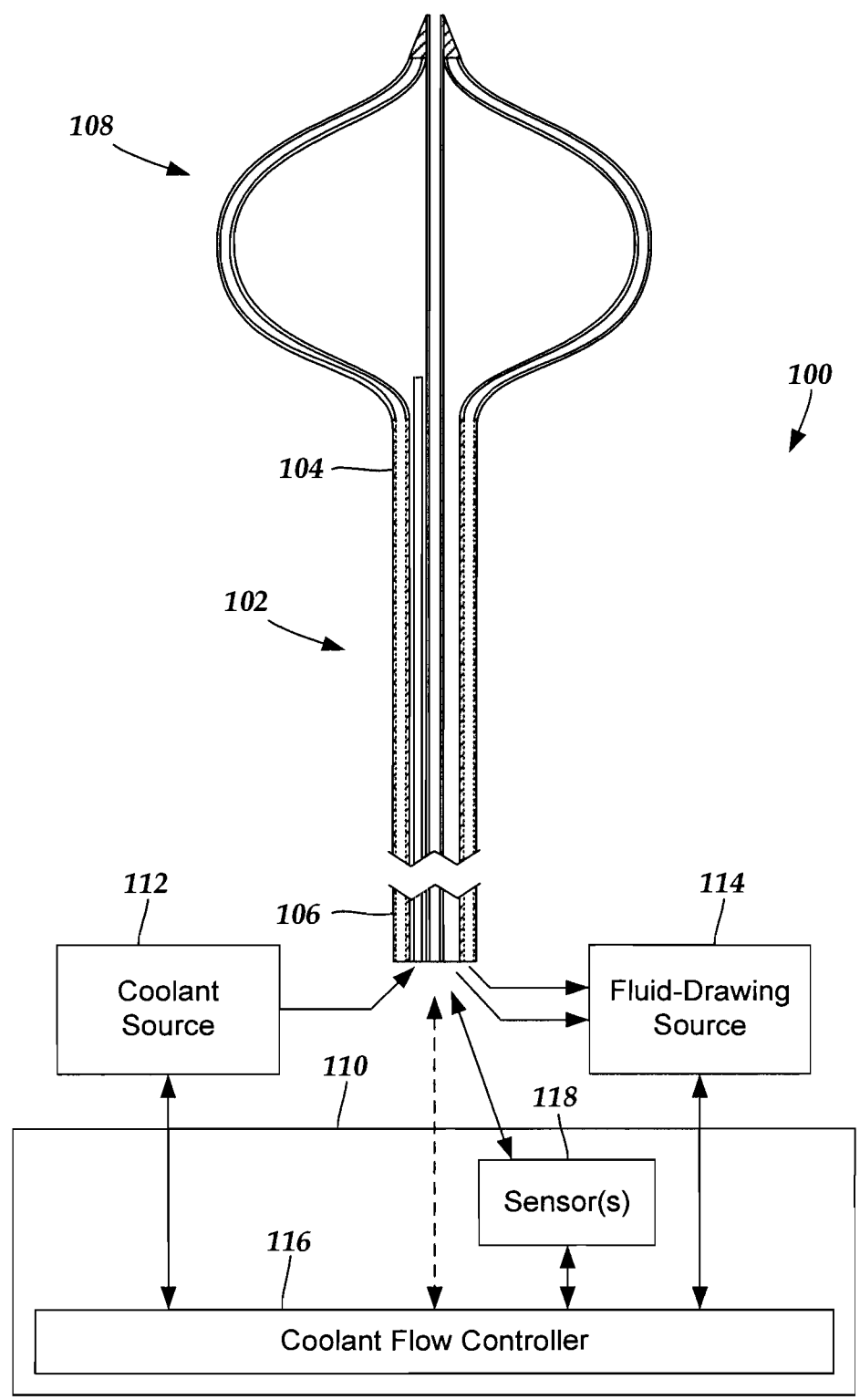
FIG. 1 is a schematic partial cross-sectional and partial block diagram view of one embodiment of a cryoablation system, according to the invention.

FIG. 1 illustrates schematically one embodiment of a cryoablation system 100. The cryoablation system 100 includes an ablation catheter 102 with a distal portion 104 and a proximal portion 106. An expansion element 108 is coupled to the distal portion 104 of the ablation catheter 102. A control module 110, a coolant source 112, and a fluid-drawing source 114 (e.g., a vacuum source, a pump, or the like) are each coupled to the proximal portion 106 of the ablation catheter 102. The control module 110 includes a coolant flow controller 116 to control the flow of coolant within the ablation catheter 102 to and from the expansion element 108. In at least some embodiments, the control module 104 also includes one or more sensors 118 for monitoring one or more conditions (e.g., pressure, temperature, or the like) within the ablation catheter 102.

In at least some embodiments, the coolant source 112 includes a coolant under pressure. A variety of different coolants may be used to provide a low enough temperature to ablate tissue upon contact. In preferred embodiments, the coolant is a low freezing point liquid with a low vaporization temperature which may be input to the ablation catheter 102 as a liquid that is sprayed into the expansion element 108, where the liquid coolant absorbs heat and is vaporized or atomized. Examples of suitable liquids include, but are not limited to, a liquefied gas (e.g., nitrogen, nitrous oxide, carbon dioxide, or the like), one or more chlorofluorocarbons, one or more hydrochlorofluorocarbons, ethanol mixtures, saline solutions, or the like. It will be understood that a combination of one or more coolants may be used in the cryoablation system 100.

Figure 2A:
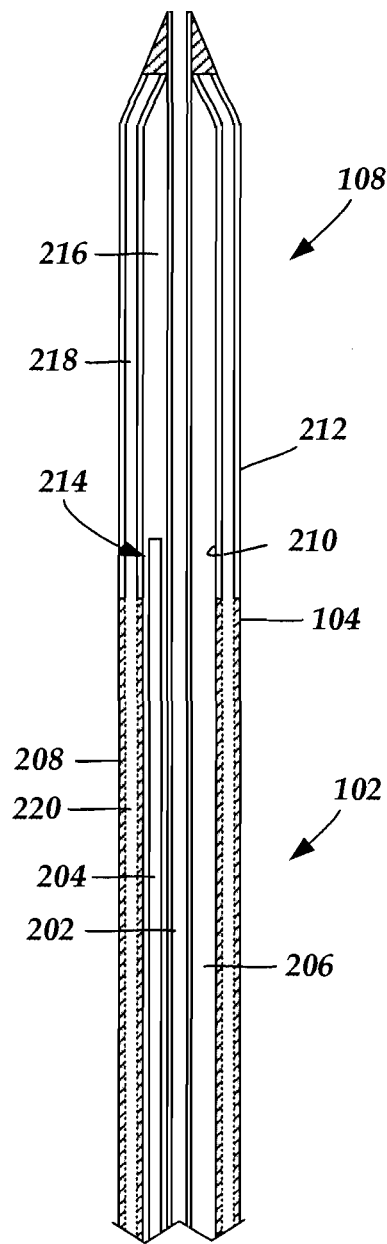
FIG. 2A is a schematic longitudinal cross-sectional view of one embodiment of an expansion element coupled to a distal portion of a catheter of the cryoablation system of FIG. 1, the expansion element in a deflated configuration, according to the invention.

During a typical cryoablation procedure, the distal portion 104 of the ablation catheter 102 is inserted into patient vasculature for delivery of the expansion element 108 to one or more ablation sites. FIG. 2A is a schematic longitudinal cross-sectional view of one embodiment of the distal portion 104 of the ablation catheter 102 and the expansion element 108. In FIG. 2A, the expansion element 210 is shown in a deflated configuration. A guide tube 202, a coolant transfer lumen 204, and at least one coolant outtake region 206 are each disposed in a flexible body 208 of the ablation catheter 102.

In some embodiments, the expansion element 108 includes a single layer. In other embodiments, the expansion element 108 includes multiple layers. For example, in at least some embodiments, the expansion element 108 includes an inner layer 210 and an outer layer 212 disposed over the inner layer 210. FIGS. 1-3, 5, and 6 show the expansion element 108 having two layers. It will be understood that the expansion element 108 may, instead, only have a single layer, or may have more than two layers.

The expansion element 108 may be formed from any elastic or semi-elastic material, such as one or more thermoplastics (e.g., polyether block amide, or the like), or other plastics (e.g., nylon, urethane, or the like) that maintain elasticity over a wide range of temperatures, particularly at the temperature of the expanded coolant. In at least some embodiments, the expansion element 108 is semi-elastic, wherein the size of the expansion element 108 does not change in response to incremental changes in pressure that are below 5 psi (about $34.5 \times 10^3$ Pa).

The guide tube 202 may be formed from any flexible material (e.g., a thermoplastic, or the like) that maintains elasticity over a wide range of temperatures, particularly at the temperature of the expanded coolant. In at least some embodiments, the guide tube 202 is configured and arranged to receive a mapping catheter (see e.g., 302 in FIG. 3). In at least some embodiments, the guide tube 202 defines a lumen through which the mapping catheter 302 can be extended. In at least some embodiments, the mapping catheter 302 is extendable from a distal end of the guide tube 202, as discussed in more detail below, with respect to FIG. 3.

The guide tube 202 is optionally configured and arranged to receive a stiffening member (e.g., a stylet, or the like) to facilitate guiding of the ablation catheter 102 to a target location within patient vasculature by providing additional rigidity to the ablation catheter 102. In at least some embodiments, the guide tube 202 defines a lumen through which the stiffening member can be extended. In at least some embodiments, the guide tube extends along a longitudinal length of the ablation catheter 102 from the proximal portion (106 in FIG. 1) of the ablation catheter 102 to a position that is beyond the distal portion 104 of the ablation catheter 102.

The coolant transfer tube 204 extends along the longitudinal length of the ablation catheter 102 from the proximal portion (106 in FIG. 1) of the ablation catheter 102. The coolant transfer tube 204 defines a lumen. A proximal end of the lumen is coupled to the coolant source (112 in FIG. 1). The coolant transfer tube 204 includes a distal end 214 that opens into the expansion element 108.

The coolant outtake region 206 is configured and arranged to accommodate coolant exiting the expansion element 108. The coolant outtake region 206 extends along the longitudinal length of the ablation catheter 102 from the proximal portion (106 in FIG. 1) of the ablation catheter 102 to the expansion element 108. In some embodiments, the coolant outtake region 206 includes one or more tubes that define one or more lumens. In other embodiments, the coolant outtake region 206 includes one or more open regions within the body 208 of the ablation catheter 102 and exterior to the guide tube 202 and the coolant transfer tube 204.

In at least some embodiments, a proximal end of the expansion element 108 couples to the distal portion 104 of the ablation catheter 102. In at least some embodiments, the distal end of the expansion element 108 is coupled to the guide tube 202. In at least some embodiments, the expansion element 108 defines an intra-expansion-element space 216 within the inner layer 210. In at least some embodiments, the intra-expansion-element space 216 is in fluid communication with the distal end of the coolant transfer tube 204. In at least some embodiments, the intra-expansion-element space 216 is in fluid communication with the at least one coolant outtake region 206. In at least some embodiments, the distal end 214 of the coolant transfer tube 204 extends beyond the distal portion of the ablation catheter 102 and into the intra-expansion-element space 216. In at least some embodiments, the intra-expansion-element space 216 is in fluid communication with the fluid-drawing source (114 in FIG. 1) via a proximal end of the coolant outtake region 206.

In at least some embodiments, a vacuum is maintained in a space between the inner layer 210 and the outer layer 212 (i.e., in an inter-expansion-element space 218) of the expansion element 108. In at least some embodiments, the inter-expansion-element space 218 is also in fluid communication with the fluid-drawing source 114 via a fluid pathway 220. In FIG. 2A, the fluid pathway 220 is shown as a space within the body 208 of the ablation catheter 102. In at least some embodiments, the fluid pathway 220 extends beyond the ablation catheter 102. In at least some embodiments, the fluid pathway 220 extends into a handle (not shown) configured and arranged to couple to the proximal end 106 of the ablation catheter 102. In at least some embodiments, the fluid pathway 220 extends to the fluid-drawing source (114 in FIG. 1). In at least some embodiments, the fluid pathway 220 is in fluid communication with the coolant outtake region 206. In at least some embodiments, the fluid pathway 220 is in fluid communication with ambient air external to the ablation catheter 102. In at least some embodiments, the fluid pathway 220 is in fluid communication with ambient air external to a patient when the distal end 104 of the ablation catheter 102 is inserted into the patient. In at least some embodiments, the fluid pathway 220 is in fluid communication with ambient air external to the cryoablation system 100.

The distal end 214 of the coolant transfer tube 204 is configured and arranged to output coolant from the coolant transfer tube 204 to the intra-expansion-element space 216. In at least some embodiments, the distal end 214 of the coolant transfer tube 204 is open. In at least some embodiments, the distal end 214 of the coolant transfer tube 204 defines one or more spray apertures. In at least some embodiments, the coolant is output as a sprayed liquid that vaporizes or atomizes as the liquid is output from the distal end 214 of the coolant transfer tube 204. In at least some embodiments, when the coolant enters the intra-expansion-element space 216, the expansion element 108 absorbs heat and expands, thereby reducing the temperature of the expansion element 108 to a temperature sufficiently low enough to ablate patient tissue upon contact.

The reduction in temperature of the expansion element 108 may be due to one or more of the Joule-Thompson effect or the latent heat of vaporization. The Joule-Thompson effect describes the cooling effect that comes about when a compressed non-ideal gas expands into a region of low pressure (e.g., within the expansion element 108). The latent heat of vaporization describes heat being released as a result of the phase change from a liquid to a gas (e.g., the liquefied coolant vaporizing upon entering the expansion element 108).

Figure 2B:
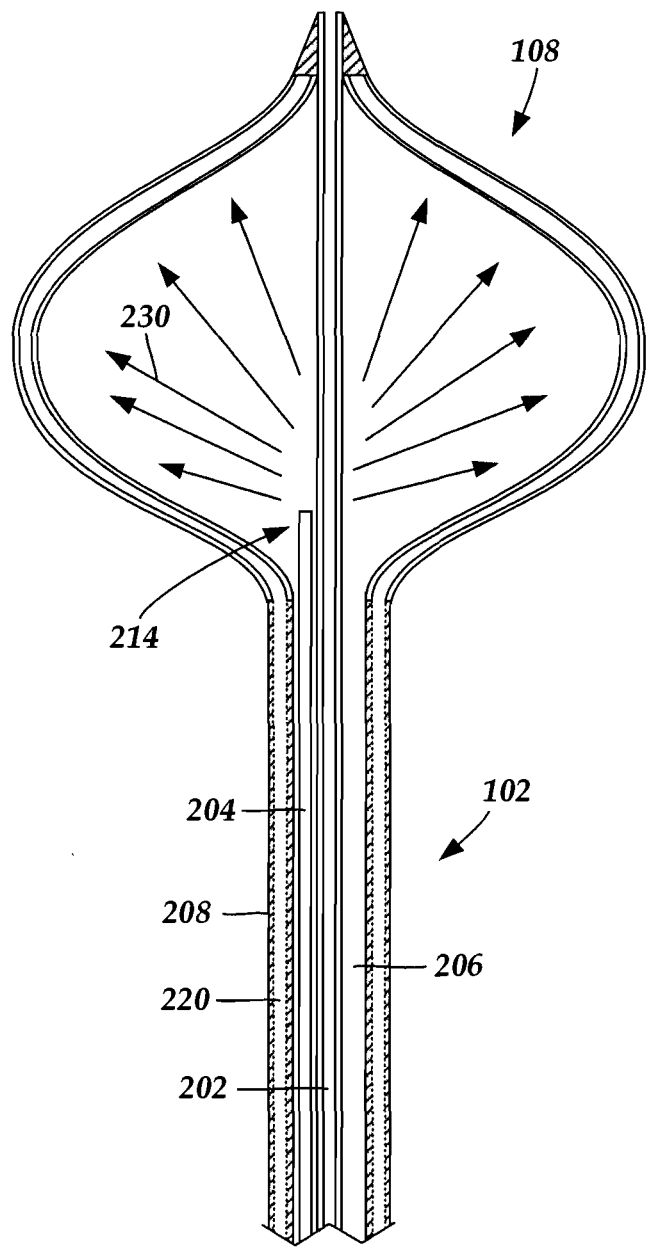
FIG. 2B is a schematic longitudinal cross-sectional view of one embodiment of an expansion element coupled to a distal portion of a catheter of the cryoablation system of FIG. 1, the expansion element an inflated configuration, according to the invention.

FIG. 2B is a schematic longitudinal cross-sectional view of one embodiment of the expansion element 108 in an inflated configuration. Directional arrows, such as arrow 230, show the flow of coolant from the distal end 214 of the coolant transfer tube 204 to the intra-expansion-element space 216. The expanded gas dissipates down the ablation catheter 102 along the coolant outtake region 206. In at least some embodiments, the fluid-drawing source (114 in FIG. 1) is used to draw the expanded, heated, and gaseous coolant along the coolant outtake region 206 from the expansion element 108 out the proximal end of the coolant outtake region 206. In at least some embodiments, the fluid-drawing source 114 is also used to maintain a vacuum in the inter-expansion-element space 218. In at least some embodiments, the fluid-drawing source 114 maintains a vacuum in the inter-expansion-element space 218 via the fluid pathway 220.

The ablation catheter 102 may be inserted in patient vasculature and guided to an ablation site, such as the ostia of one or more of the pulmonary veins in the left atrium of the heart of the patient. In at least some embodiments, the expansion element 108 is maintained in a vacuum during insertion. Sometime after the expansion element is in proximity to the ablation site, coolant from the coolant source (106 in FIG. 1) is released into the ablation catheter 102. In at least some embodiments, the coolant source 106 includes a pressurized container or pump. In at least some embodiments, the lower pressure in the expansion element 108 draws the coolant along the coolant transfer tube 104 and into the expansion element 108. In at least some embodiments, the fluid-drawing source (114 in FIG. 1) may be used to control the rate of flow of the coolant within the ablation catheter 102. The rate of flow of the coolant within the ablation catheter 102 may be adjusted to a rate appropriate to the specific type of operation.

Inserting medical devices, such as the ablation catheter 102, into patient vasculature poses an inherent risk of a breach of an outer surface of the medical device. For example, one or more openings may develop along an outer surface of the device (e.g., a hole in the body 208 of the ablation catheter 102, or the like). Exposure of inner portions of a medical device to a surrounding patient environment (e.g., patient vasculature) may result in an undesirable exchange of one or more fluids disposed within the medical device with one or more bodily fluids (e.g., blood, saliva, lymph fluid, cerebrospinal fluid, pleural fluid, cerumen, mucus, or the like).

In at least some embodiments, a medical device (e.g., an ablation system, a catheter-based medical device, or the like) that is configured and arranged for insertion into a patient includes a conductive-fluid detector disposed within the medical device. The conductive-fluid detector detects the presence of conductive fluid within a comparatively non-conductive environment of the medical device. For example, in at least some embodiments, the conductive-fluid detector can be used to detect the presence of blood in a stream of non-conductive coolant (e.g., nitrogen, nitrous oxide, carbon dioxide, or the like or combinations thereof) in either a gaseous or liquid state. It will be understood that the conductive-fluid detector can be used to detect other conductive fluids, such as drugs, water, saline, or the like or combinations thereof.

The conductive-fluid detector monitors one or more electrical parameters (e.g., voltage, resistance, current, or the like) within a lumen. In at least some embodiments, the conductive-fluid detector monitors the electrical parameter(s) between two electrodes disposed in a typically non-conductive fluid pathway. In at least some embodiments, the conductive-fluid detector detects decreases in the electrical parameter(s) between the electrodes. Decreases in the electrical parameter(s) between the electrodes above a specified amount may indicate the presence of one or more fluids that are more conductive than the environment between the electrodes (e.g., blood in a coolant stream, salt water in fresh water (or ambient air), or the like). For example, when the conductive-fluid detector is disposed in a catheter-based medical device that is inserted into a patient, the conductive-fluid detector can be used to detect an undesired breach in an inserted portion of the catheter that allows patient blood to enter into the catheter.

In at least some embodiments, one or more conductive-fluid detectors can be disposed along one or more lumens of a catheter-based medical device. For example, in at least some embodiments one or more conductive-fluid detectors can be disposed in the cryoablation system 100. The conductive-fluid detector(s) may be disposed in any suitable location within the cryoablation system 100. In at least some embodiments, a conductive-fluid detector is disposed in the body 208 of the ablation catheter 102. In at least some embodiments, a conductive-fluid detector is disposed in the coolant outtake region 206. In at least some embodiments, a conductive-fluid detector is disposed in the fluid pathway 220. In at least some embodiments, a conductive-fluid detector is disposed in the guide tube 202. In at least some embodiments, a conductive-fluid detector is disposed in the coolant transfer tube 204. In at least some embodiments, a conductive-fluid detector is disposed in the proximal 208 end of the ablation catheter 102. In at least some embodiments, a conductive-fluid detector is disposed in a portion of the ablation catheter 102 that remains external to the patient during a procedure, such as a handle (not shown), or a portion of the medical device positioned proximal to the handle.

Figure 3:
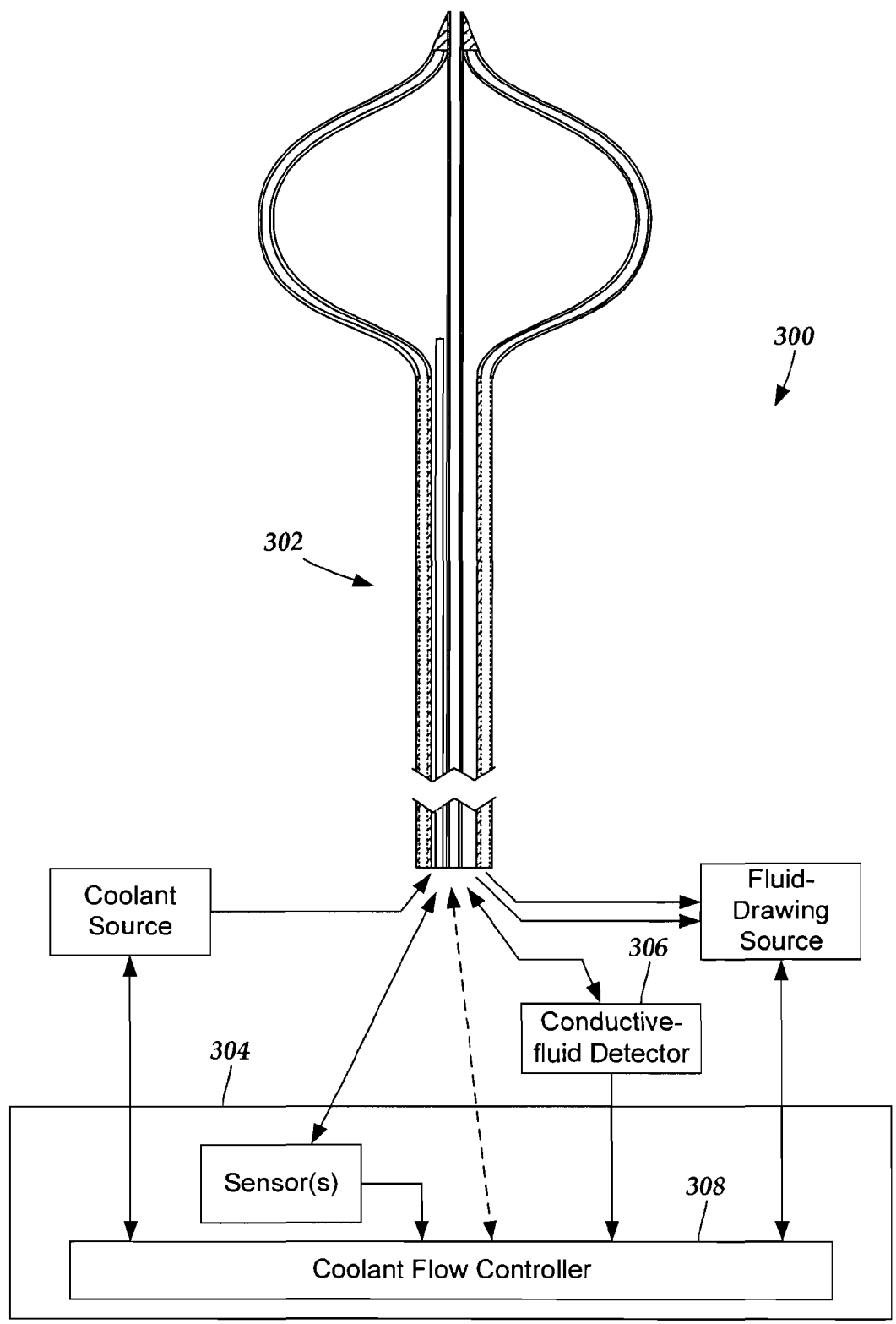
FIG. 3 is a schematic partial cross-sectional and partial block diagram view of one embodiment of a cryoablation system that includes a conductive-fluid detector, according to the invention.

FIG. 3 is a schematic partial cross-sectional and partial block diagram view of one embodiment of an ablation system 300 that includes an ablation catheter 302, a control module 304, and a conductive-fluid detector 306. In at least some embodiments, the conductive-fluid detector 306 is coupled to a coolant flow controller 308. In at least some embodiments, when the conductive-fluid detector 306 determines the presence of conductive-fluid, a signal is transmitted to the coolant flow controller 308 to reduce, or even cease, coolant flow. In at least some embodiments, when the conductive-fluid detector 306 determines the presence of conductive-fluid, power is cut to the ablation system 300. In at least some embodiments, when the conductive-fluid detector 306 determines the presence of conductive-fluid, one or more warning indicators are provided to a user (e.g., one or more audible signals, visible signals, or the like or combinations thereof).

In at least some embodiments, a conductive-fluid detector includes two electrodes disposed within a fluid pathway such that the two electrodes are in close proximity to one another, yet are separated from one another. In at least some embodiments, the electrodes are positioned in-line within the fluid pathway. The fluid pathway can be any suitable fluid pathway, such as a lumen of a catheter, in fluid communication with an insertable medical device (e.g., an ablation system, or the like). In at least some embodiments, the fluid pathway includes one or more lengths of elongated bodies defining lumens within which the electrodes are disposed. In at least some embodiments, at least one of the elongated bodies is a portion of the medical device within which the conductive-fluid detector is disposed. For example, when the medical device is the cryoablation system 100, one of the elongated bodies of the fluid pathway of the conductive-fluid detector may be the ablation catheter 102. In at least some embodiments, one of the elongated bodies of the fluid pathway of the conductive-fluid detector may be one or more bodies within the ablation catheter 102 including, for example, the coolant outtake region 206, the fluid pathway 220, the guide tube 202, the coolant transfer tube 204. It will be understood that more than one conductive-fluid detector may be disposed in a fluid pathway of a medical device (e.g., a lumen of a catheter, or the like) along either a single length of a body or along a plurality of bodies.

Figure 4A:
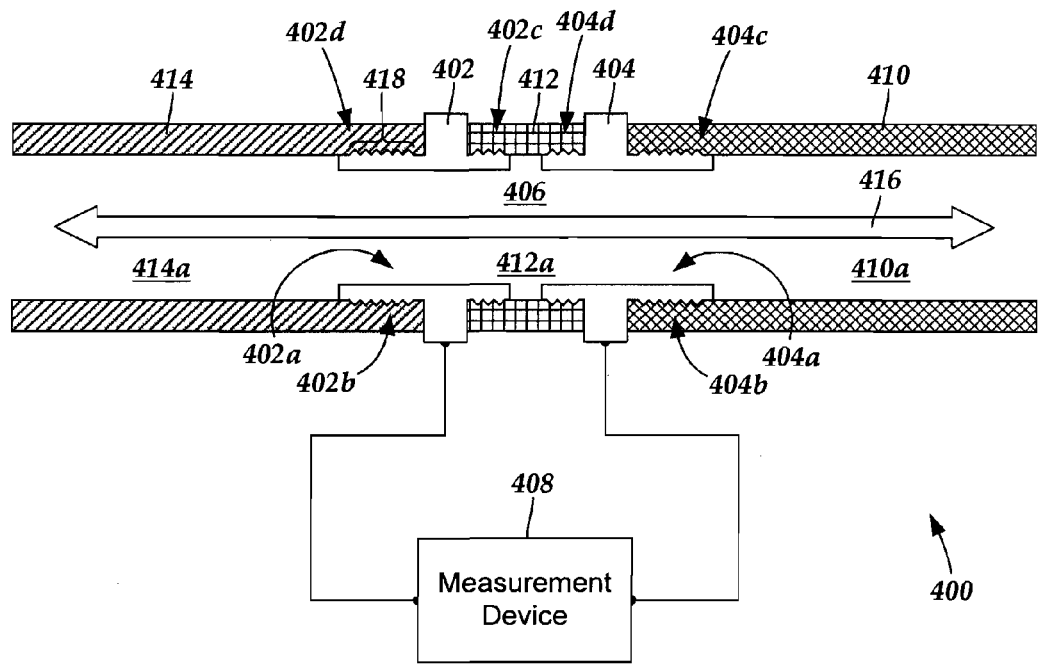
FIG. 4A is a schematic longitudinal cross-sectional view of one embodiment of a conductive-fluid detector configured and arranged for use with a medical device that is insertable into a patient, according to the invention.

The electrodes are electrically coupled or coupleable to a measurement device that measures one or more electrical parameters between the two electrodes within the fluid pathway of the ablation system 300. FIG. 4A is a schematic longitudinal cross-sectional view of one embodiment of a conductive-fluid detector 400 configured and arranged for use with a medical device that is insertable into a patient (e.g., the ablation system 300, or the like). The conductive-fluid detector 400 includes two electrodes 402 and 404 disposed along a fluid pathway 406 (e.g., a lumen defined in a catheter-based medical device, or the like), and a measurement device 408 electrically coupled to the electrodes 402 and 404.

In at least some embodiments, the electrodes 402 and 404 each include an inner surface 402a and 404a, an outer surface 402b and 404b, a distal end 402c and 404c, and a proximal end 402d and 404d. The fluid pathway includes one or more bodies. In at least some embodiments, the fluid pathway 406 includes a first elongated body 410, a second elongated body 414, and a connecting body 412. Each body of the fluid pathway 406 defines a lumen 410a, 414a, and 412a, respectively, through which one or more fluids may be contained. The one or more fluids may have a bulk flow in either direction along the fluid pathway 406, as shown by two-headed directional arrow 416.

In at least some embodiments, the conductive-fluid detector 400 can be incorporated into an elongated body of a medical device (e.g., a lumen defined in a catheter-based medical device, or the like). In at least some embodiments, the conductive-fluid detector 400 is incorporated into an elongated body of a medical device that borders a surface of the medical device that is exposed to patient tissue. In at least some embodiments, the conductive-fluid detector 400 is incorporated into an elongated body of a medical device that defines a lumen in which conductive fluids typically are not disposed. In at least some embodiments, one or more of the first elongated body 410, the second elongated body 414, and the connecting body 412 may be an elongated body of an ablation system (e.g., the cryoablation catheter 102, the coolant outtake region 206, the fluid pathway 220, the guide tube 202, the coolant transfer tube 204, or the like).

In at least some embodiments, the conductive-fluid detector 400 can be installed in an already-existing medical device by disposing the electrodes 402 and 404 and the connecting body 412 at one end of a selected elongated body of the medical device. In at least some embodiments, the conductive-fluid detector 400 can be installed in the already-existing medical device by positioning the conductive-fluid detector 400 at one end of the selected elongated body. In at least some embodiments, the conductive-fluid detector 400 can be installed in the already-existing medical device by removing a portion from the selected elongated body (e.g., a portion of tubing, a catheter, or the like) of the medical device and replacing the removed portion with the electrodes 402 and 404 and the connecting body 412.

In at least some embodiments, the outer surface 402b and 404b of the electrodes 402 and 404 are coupled to inner walls of the fluid pathway 406. The outer surfaces 402b and 404b of the electrodes 402 and 404, respectively, may be coupled to the inner walls of the fluid pathway 406 in any suitable manner. For example, in at least some embodiments, the outer surfaces 402b and 404b of the electrodes 402 and 404, respectively, are coupled to the inner walls by one or more adhesives. In at least some embodiments, at least one of the outer surfaces 402b and 404b of the electrodes 402 and 404, respectively, includes one or more barbs, such as barbs 418, that extend into one or more of the inner walls of the fluid pathway 406 without piercing the walls of the fluid pathway 406. In at least some embodiments, the outer surface 402b and 404b of the electrodes 402 and 404 are coupled to inner walls of the fluid pathway 406 such that a watertight seal is formed between the outer surface 402b and 404b of the electrodes 402 and 404 and the inner walls of the fluid pathway 406. In at least some embodiments, the outer surface 402b and 404b of the electrodes 402 and 404 are coupled to inner walls of the fluid pathway 406 such that an airtight seal is formed between the outer surface 402b and 404b of the electrodes 402 and 404 and the inner walls of the fluid pathway 406.

The bodies 410, 412, and 414 of the fluid pathway 406 may be formed from any suitable non-conductive material including, for example, plastics (e.g., polyvinyl chloride, fluorinated ethylene propylene, polyetheretherketone, or the like), and rubbers (e.g., latex, silicone, or the like) or the like or combinations thereof. The electrodes 402 and 404 may be formed in any shape suitable for coupling to the inner walls of the fluid pathway 406. In at least some embodiments, at least one of the electrodes 402 and 404 is annular. In at least some embodiments, at least one of the electrodes 402 and 404 is C-shaped. In at least some embodiments, at least one of the electrodes 402 and 404 is U-shaped. In at least some embodiments, at least one of the electrodes 402 and 404 is arced.

In at least some embodiments, the distal end 404c of the outer surface 404b of the electrode 404 is coupled to a proximal end of an inner wall of the first elongated body 410. In at least some embodiments, the proximal end 404d of the outer surface 404b of the electrode 404 is coupled to a distal end of an inner wall of the connecting body 412. In at least some embodiments, the distal end 402c of the outer surface 402b of the electrode 402 is coupled to a proximal end of the inner wall of the connecting body 412. In at least some embodiments, the proximal end 402d of the outer surface 402b of the electrode 402 is coupled to a distal end of an inner wall of the second elongated body 414.

The electrodes 402 and 404 are separated from one another by a given distance. In at least some embodiments, the electrodes 402 and 404 are separated from one another by a distance of no less than 0.05 inches (approximately 0.1 cm). In at least some embodiments, the electrodes 402 and 404 are separated from one another by a distance of no greater than 0.1 inches (approximately 0.3 cm). In at least some embodiments, the electrodes 402 and 404 are separated from one another by a distance of no greater than 0.15 inches (approximately 0.4 cm). In at least some embodiments, the electrodes 402 and 404 are separated from one another by a distance of no greater than 0.2 inches (approximately 0.5 cm). In at least some embodiments, the electrodes 402 and 404 are separated from one another by a distance of no greater than 0.3 inches (approximately 0.8 cm).

The conductive-fluid detector 400 measures one or more electrical parameters, such as resistance, current, or voltage, and detects when the measured electrical parameter goes above (e.g., in the case of current) or below (e.g., in the case of resistance or voltage) a threshold value or changes by a threshold amount. It is presumed that the increasing (e.g., in the case of current) or lowering of the electrical parameter correlates to the presence of a conductive fluid within the fluid pathway. In at least some embodiments, the conductive fluid may be undesired (e.g., patient blood in an otherwise non-conductive coolant stream). In at least some embodiments, the conductive fluid lowers the electrical parameter by forming a conductive path (e.g., a pool, stream, vapor trail, or the like) between the electrodes 402 and 404 disposed within the fluid pathway. In at least some embodiments, the conductive fluid mixes with an already-existing conductive path between the electrodes 402 and 404 disposed within the fluid pathway. It will be understood that neither the orientation nor the direction of fluid flow containing the conductive fluid is relevant to detection of the presence of the conductive fluid.

Figure 4B:
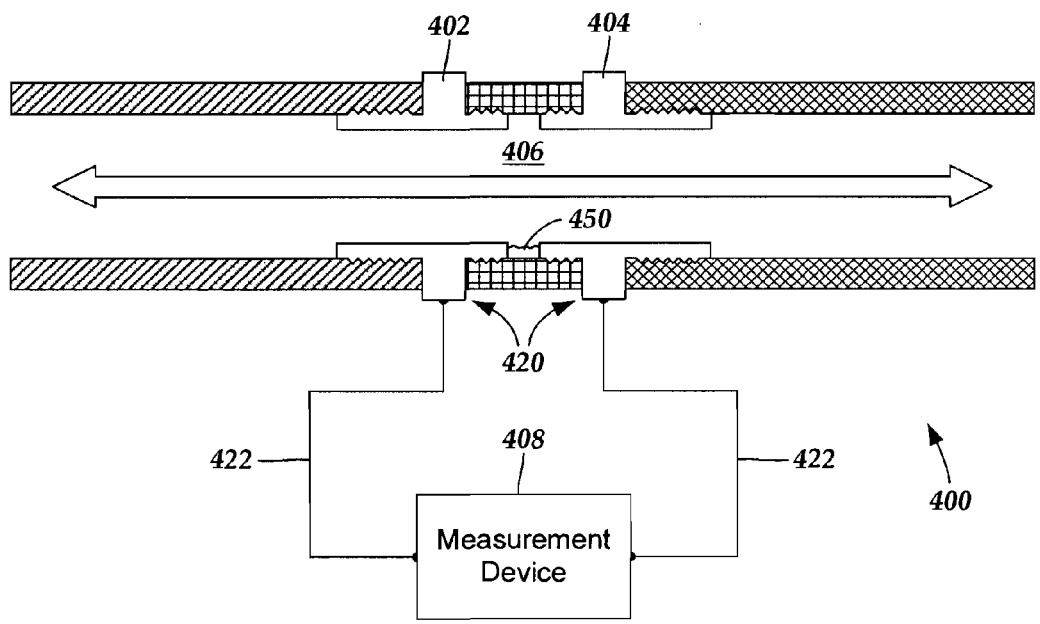
FIG. 4B is a schematic longitudinal cross-sectional view of one embodiment of a pool disposed in the conductive-fluid detector of FIG. 4A, the pool including at least some conductive fluid, according to the invention.

FIG. 4B is a schematic longitudinal cross-sectional view of one embodiment of a pool 450 that contains conductive fluid and that is disposed in the conductive-fluid detector 400 such that the conductive fluid electrically couples the electrodes 402 and 404 of the conductive-fluid detector 400 to one another. In some embodiments, the pool 450 is formed mostly from a conductive fluid (e.g., blood in a non-conductive vapor). In other embodiments, the pool contains some conductive fluid mixed in with a non-conductive liquid such that conductive fluid makes that non-conductive pool more conductive (e.g., blood in a non-conductive liquid). It will be understood that the conductive-fluid detector 400 can be used to detect conductive fluid even when the conductive fluid does not form a pool between the electrodes 402 and 404. For example, the conductive-fluid detector 400 can be used to detect conductive fluid when one or more of the conductive fluid(s) and the non-conductive fluid(s) are in a stream or a vapor.

The conductive fluid may cause the measured electrical parameter(s) to go below a threshold value when the conductive fluid is present above a given amount, concentration, conductivity, percentage, or the like. Many other factors may affect when the conductive fluid causes the measured electrical parameter(s) to go below a threshold value (or change by a threshold amount) including, for example, the amount of distance between the electrodes 402 and 404, the shape of the connecting body 412, the orientation of the connecting body 412, the material(s) used to form the connecting body 412, the shape of the electrodes 402 and 404, the orientation of the electrodes 402 and 404, the viscosity of one or more of the fluids, the flow rate of the fluid, and the like or combinations thereof.

When the conductive-fluid detector 400 is disposed in a medical device, it may be an advantage, when applicable, to dispose the electrodes 402 and 404 into the medical device such that at least a portion of each of the electrodes 402 and 404 is disposed in a portion of the medical device where liquids (e.g., blood) may accumulate, if present, during use of the medical device. For example, it may be an advantage to position the conductive-fluid detector 400 along a portion of an elongated body into which gravity, a certain motion, or the like, may cause a liquid to stream across or pool up during use. Likewise, when non-annular electrodes are used, it may be an advantage to orient the electrodes within the fluid pathway 406 to take advantage of potential fluid streaming or pooling due to gravity, motion, or the like during use.

Figure 5:
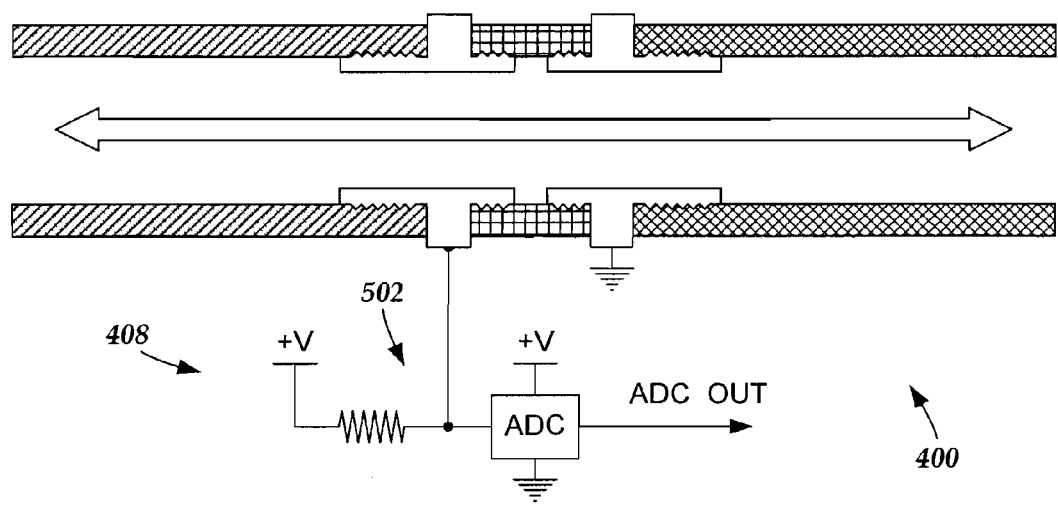
FIG. 5 is a schematic longitudinal cross-sectional view of one embodiment of a voltage divider coupled to electrodes of the conductive-fluid detector of FIG. 4A, according to the invention.

The measurement device 408 can be any measuring device (e.g., a ohmmeter, multimeter, ammeter, Wheatstone bridge, voltage divider, oscilloscope, or the like or combinations thereof) suitable for measuring one or more electrical parameters (e.g., voltage, current, resistance, or the like) between the electrodes 402 and 404 (see e.g., voltage divider 502 of FIG. 5). In at least some embodiments, the electrodes 402 and 404 include connectors 420 for electrically coupling the electrodes 402 and 404 to the measurement device 408. In some embodiments, the connectors 420 are disposed in a lumen of the fluid pathway 406. In other embodiments, the connectors 420 are disposed external to the fluid pathway 406.

In some embodiments, the measurement device 408 is coupled to the electrodes 402 and 404 via conductors 422 electrically coupled (e.g., via soldering, welding, crimping, clamping, or the like or combinations thereof) to the electrodes 402 and 404. In at least some embodiments, at least a portion of the conductors 422 are sealed to prevent short-circuiting in the presence of one or more liquids. In other embodiments, the electrodes 402 and 404 couple to the measurement device 408 via a circuit board (not shown). In at least some embodiments, at least a portion of the conductors (or circuit board) are disposed external to the fluid pathway 406, but not in direct contact with patient tissue. For example, at least a portion of one or more of the connectors 420 and the conductors (or circuit board) that are disposed external to the fluid pathway 406 may be disposed in a sealed environment external to the fluid pathway 406, or disposed within a portion of a medical device that is not insertable into a patient.

Previous experiments have been performed using electrodes spaced apart by approximately 0.1 inch (approximately 0.3 cm) along a fluid pathway containing a continuous stream of nitrous oxide. When bovine blood was injected into the nitrous oxide stream, the resistance between the electrodes dropped significantly. The amount that the resistance dropped varied depending on the amount of bovine blood injected into the nitrous oxide stream.

Figure 6:
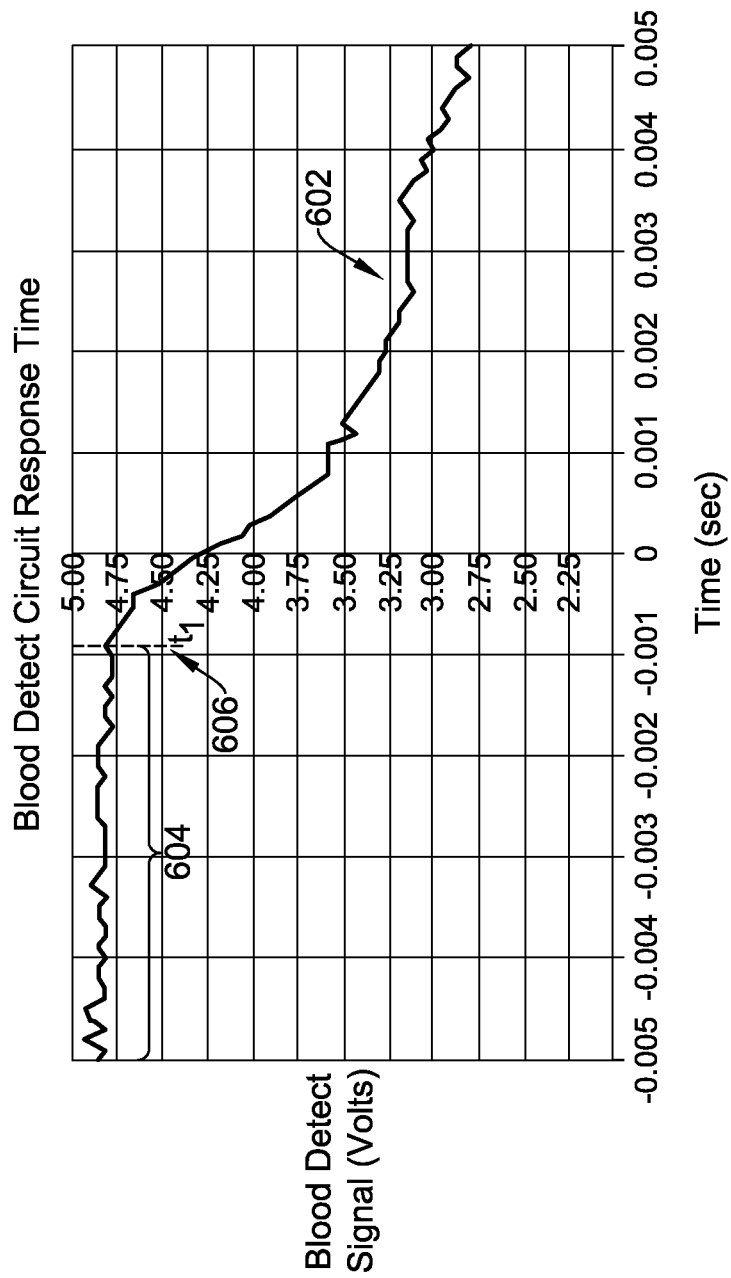
FIG. 6 is a graph plotting voltage between two electrodes of the conductive-fluid detector of FIG. 4A over time, according to the invention.

FIG. 6 is a graph plotting voltage 602 between two electrodes 402 and 404 of the conductive-fluid detector 400 over time during one particular experiment. In that experiment, the electrodes 402 and 404 were stainless steel barb fittings (part #1LLP7 from Grainger Industrial Supply, Lake Forest, Ill.) sized for 5/32 inch (approximately 0.4 cm) inner diameter polyvinyl chloride tubing. The electrodes were spaced apart by approximately 0.1 inch (approximately 0.3 cm). A continuous stream of nitrogen gas was input to a fluid pathway at a rate of 10 standard liters per minute. Bovine blood was injected into an upstream port at a rate of approximately 0.1 milliliters per second. The electrodes were electrically connected to a voltage divider and a filter. One of the electrodes was coupled to a terminal of a +5 VDC power supply through a 100 KΩ resistor, and the other of the electrodes was coupled to the other terminal of the power supply. The voltage of the electrode coupled to the 100 KΩ resistor was measured using an oscilloscope referenced to the power supply return.

In FIG. 6, during time period 604, the voltage 602 maintained a steady rate of approximately 4.8 VDC as nitrogen gas was passed across the electrodes 402 and 404. At some point in time immediately prior to time $t_1$ 606, the blood was injected into the conductive-fluid detector. At time t\ 606, enough blood was injected into the conductive-fluid detector 400 to electrically couple the electrodes 402 and 404 to one another. As shown in FIG. 6, a 1 volt decrease in voltage occurred within approximately 1.5 ms of time $t_1$ 606.

In at least some embodiments, the conductive-fluid detector 400 can be configured and arranged to detect the presence of conductive fluid in a non-conductive fluid pathway by a decrease of at least 0.2 volts. In at least some embodiments, the conductive-fluid detector 400 can be configured and arranged to detect the presence of conductive fluid in a non-conductive fluid pathway by a decrease of at least 0.3 volts. In at least some embodiments, the conductive-fluid detector 400 can be configured and arranged to detect the presence of conductive fluid in a non-conductive fluid pathway by a decrease of at least 0.4 volts. In at least some embodiments, the conductive-fluid detector 400 can be configured and arranged to detect the presence of conductive fluid in a non-conductive fluid pathway by a decrease of at least 0.5 volts.

In at least some embodiments, the conductive-fluid detector 400 can be configured and arranged to detect the presence of conductive fluid in a non-conductive fluid pathway by at least a ten percent decrease in voltage. In at least some embodiments, the conductive-fluid detector 400 can be configured and arranged to detect the presence of conductive fluid in a non-conductive fluid pathway by at least a fifteen percent decrease in voltage. In at least some embodiments, the conductive-fluid detector 400 can be configured and arranged to detect the presence of conductive fluid in a non-conductive fluid pathway by at least a twenty percent decrease in voltage. In at least some embodiments, the conductive-fluid detector 400 can be configured and arranged to detect the presence of conductive fluid in a non-conductive fluid pathway by at least a twenty-five percent decrease in voltage. In at least some embodiments, the conductive-fluid detector 400 can be configured and arranged to detect the presence of conductive fluid in a non-conductive fluid pathway by at least a ten percent decrease in voltage. In at least some embodiments, the conductive-fluid detector 400 can be configured and arranged to detect the presence of conductive fluid in a non-conductive fluid pathway by at least a thirty percent decrease in voltage.

In at least some embodiments, the conductive-fluid detector 400 can be configured and arranged to detect the presence of conductive fluid in a non-conductive fluid pathway by a decrease in resistance. For example, in the case of resistance an ohmmeter can be used to measure resistance from Megaohms down to zero ohms.

Figure 7:
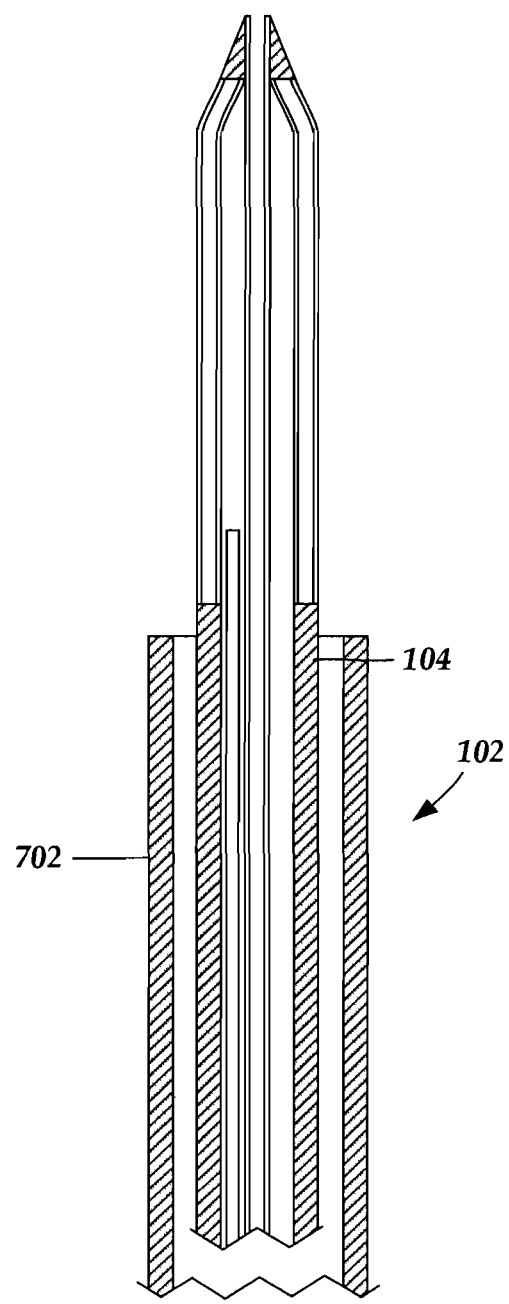
FIG. 7 is a schematic side view of one embodiment of the ablation catheter of FIG. 2A disposed in an ablation catheter which, in turn, is disposed in a sheath, according to the invention.

In at least some embodiments, a sheath may be used to facilitate guidance of the catheter through patient vasculature during insertion of the catheter. FIG. 7 is a schematic longitudinal cross-sectional view of one embodiment of the distal portion 104 of the catheter 102 disposed in a sheath 702. In at least some embodiments, the sheath 702 is steerable. Once the catheter 102 is positioned at a target location, such as the ostia of the pulmonary veins in the left atrium of the heart of the patient, the sheath 702 can be removed. When a pulmonary vein is the target location, the expansion element 108 can be expanded to occlude the lumen of the pulmonary vein. In at least some embodiments, the expansion element 108 may be expanded with a non-cryoablating fluid so as to not damage patient tissue. A contrast agent may be injected into the pulmonary vein and the region can be imaged to assess the location of the expansion element 108 and the ability of the expansion element 108 to occlude the vessel (thereby determining the potential efficacy of a cryoablation procedure by determining how well the expansion element 108 contacts the walls of the vessel). Coolant can be input to the catheter 102 to begin the tissue ablation.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A catheter-based medical device comprising:
    a catheter configured and arranged for at least partial insertion into a patient, the catheter defining at least one lumen, the at least one lumen configured and arranged to receive a first fluid; and
    a conductive-fluid detector coupled to the at least one lumen, the conductive-fluid detector configured and arranged to detect when a second fluid is disposed within the at least one lumen that is more conductive than the first fluid, the conductive-fluid detector comprising
        a first electrode having a proximal end, a distal end, and comprising an inner surface and an outer surface,
        a second electrode having a proximal end, a distal end, and comprising an inner surface and an outer surface, and
        a fluid pathway coupled to the at least one lumen of the catheter, the fluid pathway comprising a plurality of axially-separated bodies, each body having an inner surface and defining a lumen, the lumens aligned to form a shared lumen in fluid communication with the at least one lumen of the catheter, the fluid pathway configured and arranged to receive the first electrode and the second electrode, wherein the fluid pathway comprises a first elongated body having a proximal end disposed over the distal end of the outer surface of the first electrode such that the distal end of the outer surface of the first electrode couples to the inner surface of the first elongated body and the inner surface of the first electrode is disposed in the shared lumen, wherein the fluid pathway comprises a second elongated body having a distal end disposed over the proximal end of the outer surface of the second electrode such that the proximal end of the outer surface of the second electrode couples to the inner surface of the second elongated body and the inner surface of the second electrode is disposed in the shared lumen, and wherein the fluid pathway comprises a connecting body having a proximal end and a distal end, the distal end of the inner surface of the connecting body coupled to the proximal end of the outer surface of the first electrode and the proximal end of the inner surface of the connecting body coupled to the distal end of the outer surface of the second electrode such that the first electrode and the second electrode are electrically separated from one another, and the first and second elongated bodies are axially separated by the connecting body.

2. The catheter-based medical device of claim 1, wherein the outer surface of at least one of the first electrode or the second electrode comprises a plurality of barbs configured and arranged to extend into the inner surface of at least one of the first elongated body, the second elongated body, or the connecting body without piercing the first elongated body, the second elongated body, or the connecting body into which the plurality of barbs extend.

3. The catheter-based medical device of claim 1, wherein at least one of the first electrode or the second electrode is one of arced, U-shaped, C-shaped, or annular.

4. The catheter-based medical device of claim 1, wherein the outer surfaces of the first and second electrodes are coupled to the inner surfaces of the fluid pathway such that a watertight seal is formed between the outer surfaces of the first and second electrodes and the inner surfaces of the fluid pathway.

5. The catheter-based medical device of claim 1, wherein the outer surfaces of the first and second electrodes are coupled to the inner surfaces of the fluid pathway such that an airtight seal is formed between the outer surfaces of the first and second electrodes and the inner surfaces of the fluid pathway.

6. The catheter-based medical device of claim 1, wherein the conductive-fluid detector is disposed in a portion of the catheter-based medical device that is insertable into the patient.

7. The catheter-based medical device of claim 1, wherein the conductive-fluid detector is disposed in a portion of the catheter-based medical device that remains external to the patient when the catheter-based medical device is inserted into the patient.

8. The catheter-based medical device of claim 1, further comprising a measurement device electrically coupling, or coupleable to, the first electrode and the second electrode, the measurement device configured and arranged to monitor at least one electrical parameter between the first electrode and the second electrode within the lumen of the connecting body.

9. The catheter-based medical device of claim 8, wherein at least one of the first electrode or the second electrode is electrically coupled to the measurement device via an elongated conductor.

10. The catheter-based medical device of claim 9, wherein the elongated conductor extends along at least a portion of the lumen of the fluid pathway.

11. The catheter-based medical device of claim 9, wherein at least one of the first electrode or the second electrode comprise an external portion disposed externally from the shared lumen of the fluid pathway.

12. The catheter-based medical device of claim 11, wherein the external portion does not contact tissue of the patient when the catheter-based medical device is disposed in the patient.

13. The catheter-based medical device of claim 11, wherein the elongated conductor extends from the external portion of one of at least one of the first electrode or the second electrode.

14. A medical ablation device comprising:
an ablation catheter having a distal portion, a proximal portion, and a longitudinal length, the ablation catheter configured and arranged for insertion into patient vasculature, the ablation catheter comprising a body and defining at least one coolant outtake region extending along at least a portion of the ablation catheter, the at least one coolant outtake region defining at least one lumen configured and arranged to receive a coolant;
a guide tube at least partially disposed in the ablation catheter;
an ablation element coupled to the distal portion of the body of the ablation catheter, the ablation element configured and arranged for ablating patient tissue; and
a conductive-fluid detector coupled to the at least one coolant outtake region, the conductive-fluid detector configured and arranged to detect when a second fluid is disposed within the at least one lumen of the at least one coolant outtake region that is more conductive than the coolant, the conductive-fluid detector comprising:
a first electrode having a proximal end, a distal end, and comprising an inner surface and an outer surface,
a second electrode having a proximal end, a distal end, and comprising an inner surface and an outer surface, and
a fluid pathway coupled to the at least one coolant outtake region, the fluid pathway comprising a plurality of axially-separated bodies, each body having an inner surface and defining a lumen, the lumens aligned to form a shared lumen in fluid communication with the at least one lumen of the at least one coolant outtake region, the fluid pathway configured and arranged to receive the first electrode and the second electrode,
wherein the fluid pathway comprises a first elongated body having a proximal end disposed over the distal end of the outer surface of the first electrode such that the distal end of the outer surface of the first electrode couples to the inner surface of the first elongated body and the inner surface of the first electrode is disposed in the shared lumen,
wherein the fluid pathway comprises a second elongated body having a distal end disposed over the proximal end of the outer surface of the second electrode such that the proximal end of the outer surface of the second electrode couples to the inner surface of the second elongated body and the inner surface of the second electrode is disposed in the shared lumen, and
wherein the fluid pathway comprises a connecting body having a proximal end and a distal end, the distal end of the inner surface of the connecting body coupled to the proximal end of the outer surface of the first electrode and the proximal end of the inner surface of the connecting body coupled to the distal end of the outer surface of the second electrode such that the first electrode and the second electrode are electrically separated from one another, and the first and second elongated bodies are axially separated by the connecting body.

15. A medical ablation system comprising:
the medical ablation device of claim 14;
a measurement device electrically coupling, or coupleable to, the first electrode and the second electrode, the measurement device configured and arranged to monitor at least one electrical parameter between the first electrode and the second electrode within the lumen of the connecting body; and
a control module coupled to the ablation catheter and to the measurement device, the control module configured and arranged for controlling the ablation element and the measurement device.

16. The medical ablation system of claim 15, wherein the medical ablation system is one of a cryoablation system or a radio frequency ablation system.

17. A method of detecting blood in a catheter-based medical device, the method comprising:
inserting at least a portion of the catheter-based medical device into a patient, the catheter-based medical device comprising a catheter that defines at least one lumen and a conductive-fluid detector coupled to the lumen, the conductive-fluid detector comprising:
a first electrode having a proximal end, a distal end, and comprising an inner surface and an outer surface,
a second electrode having a proximal end, a distal end, and comprising an inner surface and an outer surface, and
a fluid pathway coupled to the lumen of the catheter, the fluid pathway comprising a plurality of axially-separated bodies, each body having an inner surface and defining a lumen, the lumens of the fluid pathway aligned to form a shared lumen in fluid communication with the at least one lumen of the catheter, the fluid pathway configured and arranged to receive the first electrode and the second electrode,
wherein the fluid pathway comprises a first elongated body having a proximal end disposed over the distal end of the outer surface of the first electrode such that the distal end of the outer surface of the first electrode couples to the inner surface of the first elongated body and the inner surface of the first electrode is disposed in the shared lumen,
wherein the fluid pathway comprises a second elongated body having a distal end disposed over the proximal end of the outer surface of the second electrode such that the proximal end of the outer surface of the second electrode couples to the inner surface of the second elongated body and the inner surface of the second electrode is disposed in the shared lumen, and
wherein the fluid pathway comprises a connecting body having a proximal end and a distal end, the distal end of the inner surface of the connecting body coupled to the proximal end of the outer surface of the first electrode and the proximal end of the inner surface of the connecting body coupled to the distal end of the outer surface of the second electrode such that the first electrode and the second electrode are electrically separated from one another, and the first and second elongated bodies are axially separated by the connecting body;
passing a first fluid along the at least one lumen of the catheter such that the first fluid passes through the fluid pathway and between the first annular electrode and the second annular electrode; and
monitoring at least one electrical parameter between the first annular electrode and the second annular electrode within the lumen of the connecting body when the first fluid passes between the first annular electrode and the second annular electrode.

18. The method of claim 17, wherein monitoring at least one electrical parameter comprises monitoring at least one of voltage, resistance, or current.

19. The method of claim 17, further comprising emitting a signal when the at least one monitored electrical parameter drops below or rises above a threshold value or drops or rises by at least a threshold amount.

20. The method of claim 19, further comprising cutting power to the catheter-based medical device when the at least one monitored electrical parameter drops below or rises above a threshold value or drops or rises by at least a threshold amount.

* * * * *